United States Patent [19]

Perettie et al.

[11] 4,281,135

[45] Jul. 28, 1981

[54] PREPARATION OF HIGHLY CHLORINATED PYRIDINES

[75] Inventors: Donald J. Perettie, Midland, Mich.; Norman L. Dean, Lake Jackson, Tex.

[73] Assignee: The Dow Chemical Company, Midland, Mich.

[21] Appl. No.: 153,793

[22] Filed: May 28, 1980

Related U.S. Application Data

[63] Continuation-in-part of Ser. No. 47,514, Jun. 11, 1979, abandoned.

[51] Int. Cl.$^3$ .......................................... C07D 213/04
[52] U.S. Cl. .................................................... 546/345
[58] Field of Search ......................................... 546/345

[56] References Cited

U.S. PATENT DOCUMENTS

| | | | |
|---|---|---|---|
| 1,977,662 | 10/1934 | Wibaut et al. | 546/345 |
| 3,153,044 | 10/1964 | Zaslowsky | 546/345 |
| 3,370,062 | 2/1968 | Corran | 546/345 |
| 3,420,833 | 1/1969 | Taplin | 546/181 |
| 3,538,100 | 11/1970 | Smith | 546/345 |
| 3,555,032 | 1/1971 | Johnston | 71/94 |
| 3,732,230 | 5/1973 | Brewer et al. | 546/181 |
| 4,227,001 | 10/1980 | Dietsche et al. | 546/345 |

OTHER PUBLICATIONS

Suschitzky "Polychloroaromatic Compounds," Plenum Press, pp. 225–231 and 343–345 (1974).

*Primary Examiner*—Alan L. Rotman
*Attorney, Agent, or Firm*—S. Preston Jones; Ronald G. Brookens

[57] ABSTRACT

Highly chlorinated pyridines are prepared by reacting 2,6-dichloropyridine with chlorine at temperatures of from about 150° to about 300° C. in the presence of an aluminum, iron or silica oxide catalyst and under sufficient pressure to maintain the 2,6-dichloropyridine reactant as a liquid.

6 Claims, No Drawings

PREPARATION OF HIGHLY CHLORINATED PYRIDINES

CROSS-REFERENCE TO RELATED APPLICATION

This is a continuation-in-part of application Ser. No. 47,514 filed June 11, 1979 now abandoned.

BACKGROUND OF THE INVENTION

The present invention concerns the preparation of chlorinated pyridine derivatives.

The chlorinated pyridine derivatives of the present invention are known compounds having been previously prepared by a number of processes. These compounds, namely 2,3,5,6-tetrachloropyridine and pentachloropyridine, have uses such as herbicides, pesticides, etc., and are also employed as chemical intermediates in the preparation of other highly desired herbicide or pesticide products. Previous methods for preparing such compounds include those described in U.S. Pat. No. 3,538,100 and the prior art noted therein wherein pentachloropyridine and 2,3,5,6-tetrachloropyridine have been prepared by chlorination of liquid 2,6-dichloropyridine at temperatures of at least about 180° C. and in the presence of a metallic halide catalyst.

SUMMARY OF THE INVENTION

The present invention is directed to a process for the chlorination of 2,6-dichloropyridine which comprises reacting said 2,6-dichloropyridine, in the liquid phase, with chlorine at temperatures of from about 150° to about 300° C. in the presence of a oxide catalyst.

By following the procedure of the present process, difficult process techniques are avoided. Additionally, 2,6-dichloropyridine is an economical reactant, which is obtained in significant quantities as a by-product in the production of 2-chloropyridine. Furthermore, high yields of 2,3,5,6-tetrachloropyridine and pentachloropyridine are obtained with minor amounts of other chlorinated products.

The process of the present invention can be carried out at super atmospheric pressures of from about 25 psi to about 300 psi or higher. The only limitation on the process is that the 2,6-dichloropyridine must be in the liquid state. Preferably, the process is carried out under substantially anhydrous conditions.

Representative oxide catalyst which can be employed in the present process include, for example, the oxides of aluminum, silicon, iron and the like. The preferred catalysts are alumina, silica and ferric oxide.

The catalysts are used in the instant process in small but catalytic amounts. Normally this will include amounts of up to about 10 weight percent, based on the weight of the 2,6-dichloropyridine reactant. Preferably, however, the catalyst is included in amounts of from only about 0.05 to about 5 weight percent. The catalysts are quite effective and generally the lesser amount is satisfactory.

The reaction may be conducted by contacting the 2,6-dichloropyridine with chlorine in the presence of the catalyst by a slurry technique or by contacting the mixture with the catalyst over a static bed or a fluidized bed of the catalyst. The process may be conducted in a batchwise manner, a continuous manner or a cyclic batch manner in which the pentachloropyridine and symmetrical tetrachloropyridine are removed leaving the catalyst in a distillation residue or in a quantity of the reaction mixture in the reaction vessel and fresh reactants then merely introduced into the reaction vessel. In this manner, the catalyst is recovered and reused.

The instant process may be conducted in the presence of an inert solvent, if desired, but is preferably conducted neat. Suitable inert solvents include chlorinated hydrocarbons such as for example methyl chloroform, carbon tetrachloride, and the like.

The following examples will further illustrate the invention.

EXAMPLE I

To a high pressure autoclave (reactor) containing 2006 grams of liquid 2,6-dichloropyridine was suspended a stainless steel basket containing 78 grams (3.89 weight percent) alumina pellets. The temperature of the reactor was raised to ~220° C. and the pressure was maintained at about 50 psig. Chlorine gas was introduced to the reactor at a rate equivalent to 186 grams per hour for 11 hours. At the end of this time period, the reaction mixture was quenched and the product analyzed by vapor phase chromatography. The analysis showed the conversion of the 2,6-dichloropyridine to be 99.4 percent complete with the product being 53.8 percent 2,3,6-trichloropyridine, 45.35 percent 2,3,5,6-tetrachloropyridine, 0.66 percent 2,3,4,6-tetrachloropyridine and 0.70 percent pentachloropyridine.

EXAMPLES

In this series of experiments, 2,6-dichloropyridine was charged to a high pressure stainless steel autoclave and the catalyst indicated in Table I added. The autoclave was subsequently sealed, heated to reaction temperature, and pressurized with a pad of chlorine entering through a top valve. Once pressurized, chlorine gas was then continuously sparged through the reaction mixture with stirring and analytical samples taken during the course of the reaction. The data from these experiments are summarized in Table I.

TABLE I

| | | | | | | | | |
|---|---|---|---|---|---|---|---|---|
| CHLORINATION OF 2,6-DICHLOROPYRIDINE | | | | | | | | |
| | | Wt. % of Catalyst | Time in | Temp. | Pressure | % Conversion of | Yields of Chloropyridine in % of Total Product | | |
| Run No. | Catalyst | to feed | hours | °C. | PSIG | 2,6-dichloropyridine | 2,3,6-tri | 2,3,5,6-tetra | Penta |
| 1 | Fe$_2$O$_3$ | 2.0 | 11.0 | 200 | 50 | 100 | 0.429 | 94.77 | 4.27 |
| 2 | Al$_2$O$_3$ | 2.0 | 24.5 | 200 | 50 | 100 | 15.096 | 78.39 | 1.41 |
| 3 | SiO$_2$ | 2.0 | 30.8 | 200 | 50 | 100 | 0.265 | 96.08 | 4.48 |

What is claimed is:

1. A process for preparing 2,3,5,6-tetrachloropyridine and pentachloropyridine in high yields which comprises reacting 2,6-dichloropyridine with chlorine at temperatures of from about 150° to about 300° C. in the presence of a catalytic amount of an aluminum, iron or silica oxide catalyst and under sufficient pressure to maintain the 2,6-dichloropyridine reactant as a liquid and recovering the desired product.

2. The process as defined in claim 1 wherein said catalyst is present in an amount of from about 0.1 to about 20 percent by weight of the 2,6-dichloropyridine.

3. The process as defined in claim 2 wherein said catalyst is present in an amount of from about 0.1 to about 5 percent by weight of the 2,6-dichloropyridine.

4. The process as defined in claim 1 wherein the catalyst is aluminum oxide.

5. The process as defined in claim 1 wherein the catalyst is ferric oxide.

6. The process as defined in claim 1 wherein the catalyst is silica oxide.